United States Patent [19]

Raitto

[11] 4,363,329

[45] Dec. 14, 1982

[54] SYRINGE HAVING A REVERSE-TAPER BARREL

[75] Inventor: Russell G. Raitto, Fitzwilliam, N.H.

[73] Assignee: Concord Laboratories, Inc., Keene, N.H.

[21] Appl. No.: 885,496

[22] Filed: Mar. 13, 1978

[51] Int. Cl.³ .............................................. A61B 5/14
[52] U.S. Cl. ................................. 128/765; 128/218 R
[58] Field of Search ............... 128/2 F, 218 R, 218 P, 128/218 C, 234, 215, DIG. 5

[56] References Cited

U.S. PATENT DOCUMENTS

| | | | |
|---|---|---|---|
| 1,165,686 | 12/1915 | McElroy | 128/218 P |
| 2,419,401 | 4/1947 | Hinds | 128/218 R |
| 2,666,434 | 1/1954 | Ogle | 128/218 R |
| 2,972,991 | 2/1961 | Burke | 128/218 R |
| 3,013,557 | 12/1961 | Pallotta | 128/DIG. 5 |
| 3,227,161 | 1/1966 | DeLorenzo | 128/218 R X |
| 3,890,956 | 6/1975 | Moorehead | 128/2 F |
| 3,930,492 | 1/1976 | Hatsuno et al. | 128/2 F |
| 4,057,052 | 11/1977 | Kaufman | 128/2 F |

FOREIGN PATENT DOCUMENTS

| | | | |
|---|---|---|---|
| 1500009 | 9/1967 | France | 128/218 P |
| 202402 | 3/1966 | Sweden | 128/218 P |

*Primary Examiner*—John D. Yasko
*Attorney, Agent, or Firm*—Sewall P. Bronstein; George W. Neuner

[57] ABSTRACT

An improved disposable syringe for taking arterial blood samples for blood gas testing, and the like, wherein the syringe barrel has a reverse-taper section at the forward end thereof so that, in such section, the inner diameter of the barrel is progressively larger the closer it is to the forward end of the barrel. Preferably, the syringe plunger has a compressible elastomeric tip member which has a peripheral annular wiper that extends axially toward the forward end of the syringe and radially outwardly at an acute angle to the longitudinal center line of the barrel and plunger to form an excellent seal with the inner surface of the syringe barrel while at the same time providing only a gentle pressure against such surface and hence an exceptionally low resistance to axial movement of the tip member and plunger.

The syringe, preferably, also has means for preventing further forward movement of the plunger so that, when the plunger tip is moved forward to eject air and excess liquid anti-coagulant, a predetermined amount of the anti-coagulant remains in a space of predetermined volume between the plunger tip and the forward end of the syringe barrel.

8 Claims, 10 Drawing Figures

SYRINGE HAVING A REVERSE-TAPER BARREL

FIELD OF THE INVENTION

This invention relates generally to a hypodermic syringe for obtaining a sample of a body fluid, more particularly for drawing a sample from the patient's artery or vein for blood gas analysis or other testing, and for administering fluids, more particularly for administering epidural anaesthesia.

DESCRIPTION RELATING TO THE PRIOR ART

Various syringes and methods for taking blood samples from patients are known. Such samples generally have been taken by means of a syringe which includes a generally cylindrical syringe barrel having a plunger therein which, when pulled axially by an operator, creates a suction force drawing blood into the barrel through a hypodermic needle. Many tests are performed on the blood which is thus obtained from the vein of the patient. However, an increasingly important method of determining the medical status of a patient is the obtaining of arterial blood samples for testing the blood for its content of various gases. Such samples are tested for the partial pressure of oxygen, the partial pressure of carbon dioxide, the pH of the blood, the electrolyte balance, and various other tests known in the art.

Syringes previously used in obtaining arterial blood samples have generally been glass syringes, in which the cylindrical barrel is made of glass and the plunger is a ground glass rod which closely fits within the cylinder. Generally the technique for taking samples with such devices comprises, as a first step, the drawing of an anti-coagulant solution, such as sodium heparin, into the syringe to replace the air in the syringe. This solution also acts as a lubricant for the walls so that the glass plunger may move relatively freely within the cylinder. The syringe is inverted and all air is expelled from the barrel and needle, along with the bulk of the anti-coagulant solution, which is normally far in excess of the amount needed for the blood sample. It is extremely important that all air be expelled from the syringe, since one of the tests performed is the measurement of the amount of oxygen present in the blood, and even minute contamination with air will prevent accurate measurement of that amount. After suitable preparation of the patient, the hypodermic needle is inserted into the artery and blood is either forced into the syringe by the pressure of the blood in the artery or is drawn into the syringe barrel by withdrawing the plunger. One advantage of the glass syringe previously used is the ease with which the plunger may be moved within the lubricated barrel. The glass plunger is ground to very close tolerances, so that it is sufficiently close to the syringe barrel wall to prevent leakage but sufficiently far away to allow formation of a thin film of the anti-coagulant. Even very low arterial blood pressures are usually sufficient to enter the syringe and force the glass plunger backwards without any aid from the person taking the sample. Upon entry into the syringe the blood mixes with whatever anti-coagulant solution remains in the needle, syringe tip and syringe barrel after the excess has been expelled.

Glass syringes are also conventionally used in epidural anaesthesia employing the loss of resistance technique because of the low resistance to movement of the plunger in the barrel. Such techniques involves loading the syringe with 2–3 ml of normal saline, sterile distilled water or air. The needle (usually 16–18 g) is then applied to the syringe. The needle is then inserted into the back towards the spinal area in question, all the while exerting gentle pressure on the plunger. When the needle tip goes through the ligamenta flava into the potential epidural space, the loss of resistance will be immediately felt by the thumb because the fluid or air will be pushed into the space. Thereafter the syringe is removed from the inserted needle and is replaced on the needle by a syringe loaded with anaesthesia. This "loss of resistance" technique requires a syringe with an exceedingly smooth action and low resistance.

The glass syringes previously used have suffered from a number of disadvantages. They are expensive since the grinding requires close tolerances, in the order of 0.0007 inches clearance between the piston and the cylindrical syringe body. They are easily breakable, which is especially costly after the sample has been taken. The glass plunger and the glass barrel of each syringe must commonly be matched during the grinding by the manufacturer, since variations in grinding from one plunger to another may be sufficient to permit leakage of air or other material around the plunger, which will contaminate the sample. Thus the barrels and plungers cannot easily be individually mass produced since the plungers often cannot be satisfactorily interchanged one with another in any given barrel, as pointed out in U.S. Pat. No. 2,419,201 to Hinds. Further, because of the easy movement of the glass plunger in the cylinder, the plunger falls out of the barrel of its own weight, and normally breaks on the floor, unless the syringe is carried needle end down. Special metal holders for the glass barrel have been used to prevent this problem.

Attempts have been made to avoid these disadvantages by either manufacturing both the barrel and the plunger out of materials other than glass, such as plastics, or by using glass barrels with plastic plungers. In order to prevent leakage around the plunger, these syringes depend upon the use of a compressible and elastomeric tip at the end of the plunger, which tip generally has one or more ribs which are slightly larger in diameter than the inside of the barrel in their uncompressed state and which, when placed within the barrel, are deformed and compressed against the interior wall of the barrel and thereby form a seal. This type of seal, however, has made the movement of the plunger within the barrel difficult, thus normally requiring manual withdrawal of the plunger to obtain the blood sample, particularly when the patient's arterial pressure is low as is often the case. The handling of the syringe which is involved when manual withdrawal of the plunger is required may cause traumatization or collapse of the artery from which the blood is being taken.

A further major problem has been the fact that when an axial force is applied to the plunger to expel the air and excess anticoagulant solution, the compressible elastomeric tip at the end of the plunger compresses and deforms against the floor of the syringe barrel. The initial contact of the compressible and elastomeric tip with the barrel floor is at an area spaced from the central needle opening in the floor. As force continues to be applied after initial contact the tip is compressed and deformed against the floor to move the contact area radially inwardly toward the needle opening. When the plunger is released prior to the insertion of the hypodermic needle into the artery, the pressure on the compressible and elastomeric tip is also released whereby it recovers its normal shape and in so doing moves back slightly from the barrel floor until its only contact with such floor is its initial contact area thereby drawing a small amount of air into the tip of the hypodermic needle which becomes mixed with the blood sample thereby increasing its oxygen and nitrogen content. Also, air bubbles tend to collect on the forward face of the elastomeric tip particularly at the area immediately adjacent the point of contact with the syringe barrel wall. Since the samples which are drawn to test for the amount of oxygen and carbon dioxide in the blood are very small, e.g., 2, 5 or 10 ml, even minute amounts of oxygen and carbon dioxide leaked into the sample or in the form of air bubbles have potentially adverse effects on the results obtained.

The compressibility of the plunger tip also causes non-uniformity in the amount of anticoagulant left in the syringe barrel, syringe tip and hypodermic needle. As can be readily appreciated, the amount left will depend upon the amount of pressure used to expel the air and excess anticoagulant since greater pressure will compress and distort the compressible plunger tip to a greater degree, thus expelling more anticoagulant. If too little anticoagulant solution remains to be mixed with the blood, the blood may coagulate prior to testing and thus adversely affect the results obtained. If, on the other hand, too much anticoagulant solution is left in the syringe, its presence may adversely affect the test, as is known in the art.

Various disposable syringes have been described. For instance U.S. Pat. Nos. 2,972,991 and 2,666,434; Swedish Pat. No. 202,402; and French Pat. No. 1,500,009 describe disposable syringes designed primarily for injecting medicants and thus have relatively tight seals between the plunger tip and the syringe barrel. Disposable blood sampling syringes are described, for example, in U.S. Pat. Nos. 4,057,052; 3,930,492 and 3,890,956; and in my copending patent applications, U.S. Ser. No. 715,678 filed Aug. 19, 1976 and entitled "Blood Sampling Syringe" and U.S. Ser. No. 714,644 filed Aug. 16, 1976 and entitled "Syringe." These disposable blood sampling syringes employ techniques for lowering the resitance of the seal against the syringe barrel while maintaining an effective seal so that a blood sample may be drawn by filling the syringe due to the blood pressure of the patient alone. However, for certain patients with low blood pressure, the resistance due to the seal in these syringes may still be too high to enable the syringe to fill by blood pressure alone while maintaining an effective seal and the plunger may have to be withdrawn manually.

SUMMARY OF THE INVENTION

The present invention provides a disposable syringe comprising a barrel having a forward end adjacent an opening for communication with a needle and including a working section adjacent said forward end in which the inner diameter of said barrel is tapered so that the inner diameter of said barrel is larger at the forward end of said barrel and the inner diameter decreases progressively to a predetermined point defining the rearward end of said working section. The term "working section," as used herein, refers to that portion of the syringe barrel adjacent the forward end of the barrel and extending rearward to a predetermined point for a distance over which the plunger tip moves when drawing a blood sample. the syringe also comprises a plunger having a plunger stem and a generally cylindrical plunger tip having an annular, elastically deformable wiper extending peripherally to engage the inner wall of the syringe barrel, thus forming a seal. This disposable syringe is particularly suited to be used for obtaining a blood sample from a patient because of the low force requirement for the operation thereof.

The reverse taper of the working section of the syringe, among other things, provides lower static frictional forces which can be overcome by lower blood pressures and thus enable the syringe to be filled by blood pressure alone, even though a patient has low blood pressure. Because dynamic frictional forces are less than static frictional forces, once set in motion the plunger will continue until the frictional forces increase, due to the taper of the barrel wall, to a point where the frictional forces are equal to the force of the patient's blood pressure or until the plunger is stopped by external means. The taper of the working section enables lower static frictional forces yet provides an effective seal with the plunger tip which is increasingly better as the blood sample is drawn.

In one embodiment of the present invention the plunger tip comprises a compressible, elastomeric, generally cylindrical plunger tip of lesser diameter than the inner wall of the barrel, the plunger tip having an integral, annular, elastically deformable wiper extending peripherally radially outwardly and axially forwardly from said plunger tip at a forward portion thereof at an acute angle to the longitudinal center axis of the plunger tip and terminating at the outer edge thereof in a wiping edge having a minimal diameter slightly in excess of the largest diameter of the working section of the barrel, thereby forming a sealing engagement with the inner wall of the barrel, the annular wiper being the sole sealing element between the plunger tip and the barrel wall.

In another embodiment of the invention, the syringe further comprises means for limiting the rearward movement of the plunger, while drawing a blood sample, at a predetermined point to provide a predetermined sample size.

In yet another embodiment of the invention, the syringe further comprises means for preventing further forward motion of the plunger at a predetermined point to define a chamber of predetermined volume to retain a desired amount of anticoagulant in the syringe when expelling air and excess anticoagulant prior to drawing a blood sample.

DETAILED DESCRIPTION OF THE INVENTION

Figure 2:
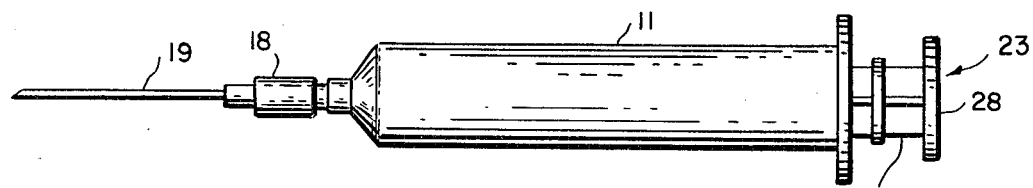
FIG. 2 is a longitudinal view of a preferred embodiment of a syringe assembly of the present invention.

Referring to the Figures of the drawings, the syringe depicted is a preferred embodiment of this invention and has a relatively rigid, generally cylindrical hollow body or barrel 10, preferably made of an inexpensive substantially transparent plastic material, such as polyethylene or polypropylene, which is inert to, i.e., does not affect, the sample to be taken, and which is substantially impermeable to oxygen and carbon dioxide. Other suitable materials, such as polystyrenes, acrylic or methacrylic polymers and various glasses, are well known in the art. The generally cylindrical barrel has a central bore and terminates at the rearward end with finger piece 12. This finger piece 12 generally has the shape of an annular flange but can be any shape which provides support for two fingers, e.g., hexagonal, or can take the form of two tabs. The barrel terminates at the forward end in an axially forwardly and radially inwardly tapered end wall which forms the tapered floor of the central bore and which extends forwardly into the reduced diameter tapered tip 16 of the barrel. As shown, barrel tip 16 is generally frusto-conical in shape. Tip 16 is shown in FIG. 2 as carrying the hypodermic needle 19 through frictional engagement of the tapered periphery thereof with the tapered end of the internal passage of cylindrical base member 18 of the needle 19. However, the needle may be secured to the tip 16 by a conventional luer lock arrangement on the base member 18 and tip 16. The forward end of the barrel has a centrally located needle opening therein which extends into the internal passage of tip 16 to communicate with the needle 19.

Figure 3:
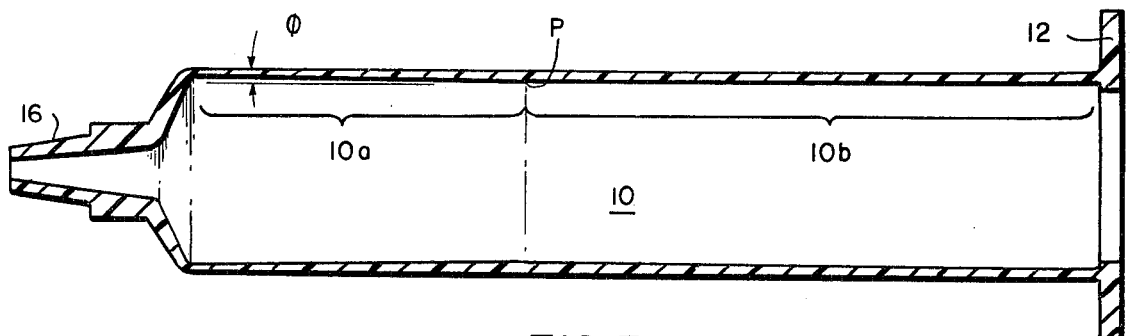
FIG. 3 is an enlarged longitudinal section of the syringe barrel of FIG. 2 illustrating the reverse-taper section.
Figure 4A:
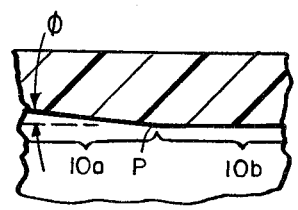
FIG. 4a is an enlarged view of the area around point P in FIG. 3.
Figure 4B:
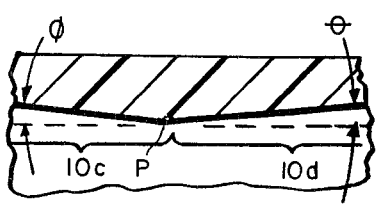
FIG. 4b is an illustration of an alternate construction for the area around point P in FIG. 3 showing the rearward portion of the syringe barrel to be tapered outwardly from point P toward the rearward end of the syringe barrel.
Figure 6:
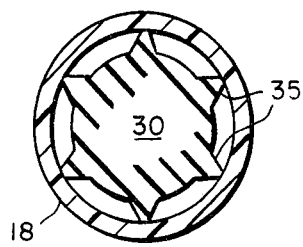
FIG. 6 is a section taken along line 6—6 in FIG. 5.
Figure 7:
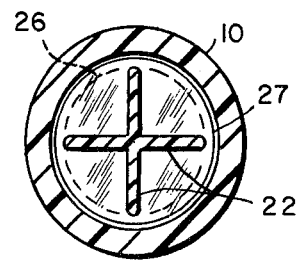
FIG. 7 is a section taken along line 7—7 in FIG. 5.

The inner wall of the barrel 10 is shown divided axially into two sections, working section 10a and the remaining section 10b. The working section 10a, i.e., the portion of the barrel 10 that is traversed by the plunger tip 30 in taking a sample, is tapered inwardly from the forward end of the barrel 10 to a predetermined point P that has a position that is selected to provide a desired sample size. Thus, in the working section 10a, the inner diameter of barrel 10 is largest at the point adjacent the forward end of the barrel and is smallest at point P. In the remaining section 10b of barrel 10 the inner diameter of the barrel can be constant as illustrated in FIGS. 3 and 4a or it can be tapered outwardly from point P to the rearward end of barrel 10 as illustrated in FIG. 4b.

Figure 1:
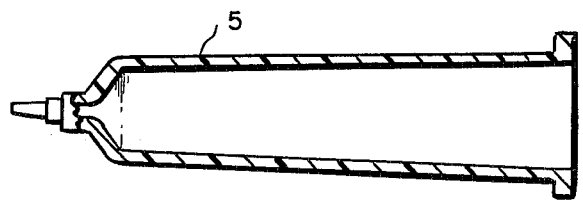
FIG. 1 is a longitudinal section of a typical prior art syringe barrel in which the diameter of the inner wall tapers (taper exaggerated) outwardly from the forward end of the barrel to the rearward end of the barrel.

It is known to taper the inner wall of the barrel outwardly from the forward end to the rearward end as illustrated in FIG. 1, for instance, to aid in molding the barrel. However, until the present invention, there has been no suggestion to taper the inner wall of the barrel inwardly from the forward end thereof rearwardly to at least a point P and, in fact, such an inward taper was thought undesirable, particularly in view of possible molding problems.

Although the amount of taper that is useful in the working section 10a of the syringe barrel 10 is dependent upon the materials from which the barrel 10 and the plunger tip 30 are made, it is preferred that the total taper over the working section 10a of barrel 10 not be greater than about 1.5 percent of the inner diameter of the barrel at point P or that the inner diameter at the forward end of the working section be no greater than about 1.5 percent more than the inner diameter at point P. In other words, if, for example, the inner diameter of barrel 10 at point P is one centimeter, the inner diameter of barrel 10 at the forward end of working section 10a should not exceed 1.015 centimeters. More preferably, the total taper over the working section of the barrel is in the range of from about 0.75 percent to about 1.5 percent of the inner diameter of the barrel at point P.

The syringe illustrated in the drawings also comprises a plunger 23 having a plunger stem 24 and a plunger tip 30. The plunger stem comprises two axial ribs 22 perpendicular to each other and a number of circular discs 26 perpendicular to the ribs 22 positioned along the axis of plunger stem 24. One of the discs 27 has a greater diameter than the other discs and functions as a stop to limit outward movement of the plunger by engagement with rib 20 at the rearward end of the syringe barrel when drawing a blood sample. The plunger can be withdrawn from the syringe barrel by exerting additional manual force to move disc 27 past rib 20. The plunger stem also has a disc 25 which is larger in diameter than disc 27 and will not move past rib 20 regardless of the force exerted. Disc 25 functions as a stop preventing further inward movement of the plunger and is positioned to prevent such further inward movement at a predetermined position of said plunger tip to form a chamber or space between the plunger tip 30 and the forward end of the syringe barrel 10. The size of the chamber or space thus formed can be predetermined to contain a desired quantity of anticoagulant. Thus disc 25 effects a positive stop preventing further inward movement and avoiding any compression of the plunger tip 30.

Disc 27 is positioned along the longitudinal axis of the plunger 23 in accord with size of sample to be drawn with the syringe, thus providing an effective preset sample size. Thus the size of the chamber formed by the plunger tip 30 and the forward end of the syringe barrel 10 can be sized to contain the precise amount of anticoagulant required for the sample size.

The plunger stem 24 is preferably made of an inexpensive plastic material, such as polyethylene or polypropylene, which is also inert to the sample to be taken. Other materials which can be used are the same materials of which the barrel is made. In fact, the plunger stem is preferably made of the same material as the barrel but it need not be. At its rearward end, stem 24 terminates in a thumb supporting flange 28. The plunger stem terminates at the other end on a head portion to which the compressible and elastomeric plunger tip is secured.

Figure 5:
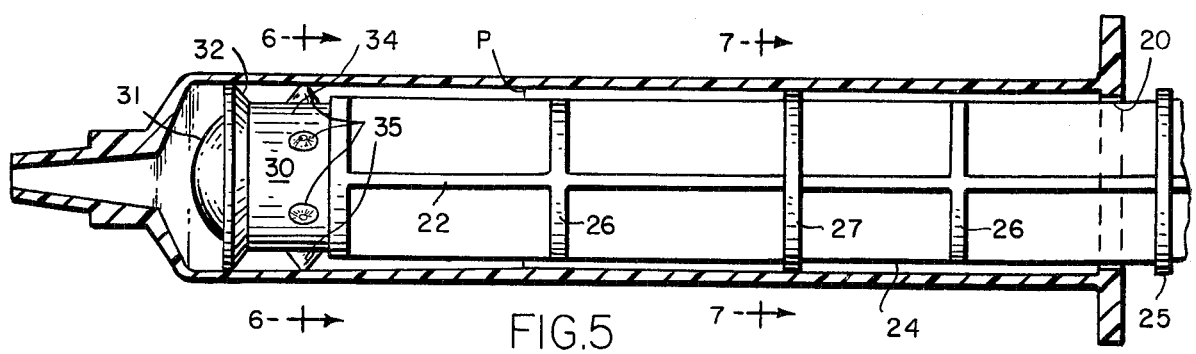
FIG. 5 is a longitudinal partial section of a preferred embodiment of a syringe of the present invention illustrating the plunger in the syringe barrel.
Figure 8:
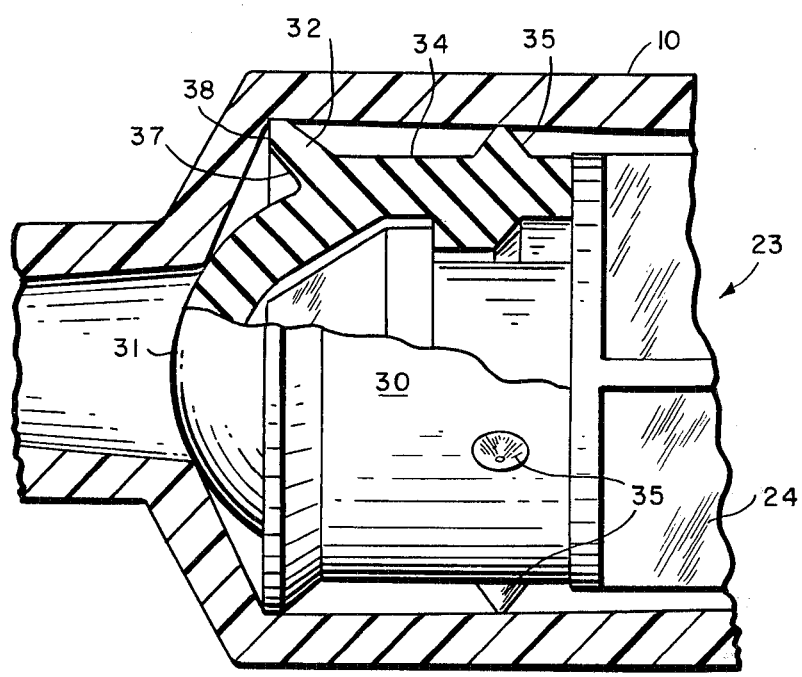
FIG. 8 is a longitudinal partial section of a part of the forward end of a preferred embodiment of a syringe of this invention illustrating the plunger tip in sealing engagement with the inner wall of the syringe barrel.
Figure 9:
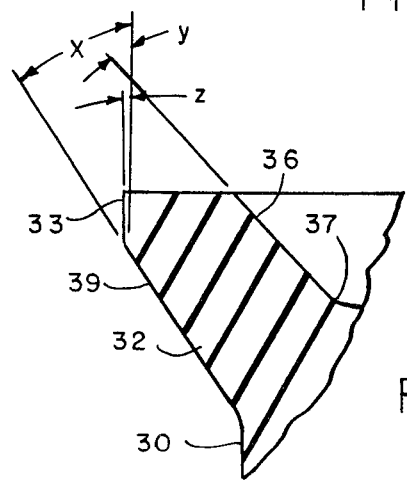
FIG. 9 is an enlarged view in section of a part (rotated so that the longitudinal axis is oriented vertically in the illustration) of the wiper of the plunger tip of FIG. 5 before it is inserted into the syringe barrel.

The plunger tip 30 is a generally cylindrical body of lesser diameter than the inner wall of the barrel 10 having at least one annular, elastically deformable wiper 32 extending peripherally to engage the inner wall of the barrel to form a seal. Preferably, the plunger tip 30 is made of a compressible, elastomeric material and has a main generally cylindrical portion 34, the periphery of the forward portion of which extends axially forwardly ("axially forwardly" and "axially inwardly" mean toward the barrel floor, whereas "axially rearwardly" and "axially outwardly" mean away from the barrel floor) and radially outwardly at an acute angle y (see FIGS. 5, 8 and 9) from the longitudinal center axis of the plunger 23 and plunger tip 30 forming an integral, annular wiper 32, the wiping edge of which is resiliently and yieldably forced into sealing engagement with the inner wall of the barrel 10. The plunger tip 30 extends axially forwardly from the base 37 of wiper 32 into a reduced diameter leading end portion 31 which has convex curvilinear shape. An annular recess or trough 38 is formed between the annular wiper 32 and the reduced diameter lending end portion 31, as shown.

The rearward end of plunger tip 30 has an internal socket in which is received the seat of the plunger stem 23 to secure the plunger tip to the end of the plunger stem.

The only part of the plunger which engages the inner wall of the barrel to form a seal is the annular wiping edge 32 which exerts only a slight force on such wall to thereby reduce frictional drag and permit the plunger to be easily moved axially in the barrel.

The acute angle y between the forward or leading wiper surface 36 (FIG. 9) of the wiper 32 and the longitudinal center axis of the plunger tip is slightly greater than the acute angle x between the rearward or trailing wiper surface 39 of the wiper and the longitudinal center axis whereby the wiper is tapered in thickness with the base 37 of the wiper being thicker than the end portion of the wiper. The thicker base strengthens the wiper whereas the tapered thinner end portion increases the flexibility of the wiper edge to provide only gentle sealing pressure on the inner barrel wall to thereby minimize resistance to axial movement of the plunger.

In its relaxed state when the plunger tip is removed from the barrel, the wiper edge 33 of the wiper 32 is of slightly greater diameter than the inner wall of the barrel 10 at least at the forward end thereof so that when the plunger tip is forced into the bore such edge 33 is forced radially inwardly about the base 37 of the wiper i.e., the wiper is bent or rocked radially inwardly about its base, against the force exerted by the elastic and compressible material, which force yieldably and with only a slight pressure urges such wiper edge into excellent sealing engagement with the inner wall, at least in the working section 10a thereof, with very little frictional drag.

In its relaxed state when the plunger tip is removed from the barrel, the wiper edge surface 33 preferably extends radially outwardly and axially forwardly at a slight angle z, e.g., about 2° to the longitudinal center axis of the plunger tip and the barrel bore. The purpose of this is to reduce the chance of leakage while still achieving gentle sealing pressure. When the plunger tip is forced into the barrel bore, this wiper edge surface 33 is forced to assume a position in which it is parallel to the inner wall of the working section 10a of the barrel. Without this slight inclination of the wiper edge surface 33, the undersized barrel may tend to bend the leading end of such wiper edge surface radially inwardly to either reduce the pressure of the wiper edge surface on the inner wall at such leading end or to cause such leading end to move slightly away from the inner wall to provide a slight space or groove therebetween which may result in leakage.

By providing this slight angle to the wiper edge surface 33, maximum sealing pressure is applied and concentrated at the leading end of surface 33 where it does the most good and over a relatively small area, thereby minimizing frictional drag. For further details regarding the preferred plunger tip construction, see copending U.S. application Ser. No. 714,644 filed Aug. 16, 1976 and entitled "Syringe," which is hereby incorporated by reference.

The plunger tip can be made of any elastomeric and compressible material with memory, which has a low coefficient of friction with the barrel wall material and which is inert to the sample material, to the anticoagulant and to any other substance which is to be located within the syringe barrel. Natural and synthetic rubbers can be used such as neoprene rubber as well as other elastomeric polymers such as polyvinyl chloride, polyurethanes, polyesters, etc. A preferred material is silicone rubber.

The elastomeric plunger tip 30 has a plurality of raised portions 35 spaced around the circumference of the rearward section of the plunger tip 30 and engaging the inner wall of the barrel 10 with minimum contact to avoid any significant frictional force. These raised portions 35 of the plunger tip 30 prevent canting of the plunger tip to maintain the plunger tip in a concentric position within the syringe barrel 10 and allow the sole wiping edge 33 of the plunger tip to maintain its most effective sealing engagement with the syringe barrel. The raised portions on the rear section of the plunger tip can be of any shape that will accomplish the purpose of preventing canting of the plunger tip. Generally, a semi-spherical, conical, or frusto-conical shape is preferred to avoid excessive frictional contact with the syringe barrel and for ease of manufacture.

Conventionally in taking a blood sample, a liquid anticoagulant, e.g., sodium heparin, to prevent coagulation of the blood sample is either drawn into the syringe before the blood sample is taken or is located in the syringe as packaged. The excess of such liquid anticoagulant and any air in the syringe is then expelled through the needle opening and needle by forward movement of the plunger and plunger tip.

The excess anticoagulant and air are expelled by moving the plunger tip to its forwardmost position. If the syringe has a means for preventing further forward motion, such as the syringe illustrated in the drawings, the chamber or space defined by the forward surface of the plunger tip and the forward end of the barrel retains a predetermined quantity of anticoagulant. If no such means for preventing further forward motion is used, a minimum amount of anticoagulant is still retained in the trough 38 formed between the annular wiper 32 and the reduced diameter leading portion 31 of the plunger tip. The size of the chamber formed when a further forward motion preventing means is used or of the trough 38 is preferably designed so that the amount of anticoagulant trapped in this space, together with the communicating passage to the needle and the needle when the plunger tip is in its forwardmost position, is sufficient to prevent coagulation of the sample taken but is less than an amount which will interfere with the testing of the sample. Accordingly, the right amount of anticoagulant is automatically assured.

Preferably the volume of the space, together with the passage communicating between the barrel 10 and the needle 19, and the needle bore, is between 0.01 and 1.0 milliliters and more preferably between 0.25 and 0.5 milliliters for every 5 milliliters of blood sample taken.

The non-compressible liquid trapped in trough acts as a non yieldable stop or barrier to reduce any deformation and compression of the plunger tip against the barrel floor radially outwardly of the narrow annular sealing area upon continued application of forward axial force on the plunger.

Whereas with a 10 cc plastic JELCO syringe and 22 gage needle a force of 64 mm/Hg was required to force the plunger back, the force required to force the plunger back with a syringe of the same size embodying the invention was only 15-18 mm/Hg, i.e., only about ¼ of the force was required. Accordingly, the syringe of the instant invention fills automatically with very low arterial pressures without manually pulling the plunger outwardly. With a needle of 22 gage, a syringe embodying the instant invention would be as responsive to hydraulic force as a glass syringe.

In spite of the very low pressure required to fill the syringe of the invention and the very gentle sealing pressure of the wiper edge against the syringe barrel, the sealing achieved is excellent by virtue of the design of the wiper. The force applied by the blood pressure tends to urge the wiping edge against the barrel wall to increase the sealing effect. The plunger tip illustrated in the drawings has withstood a hydraulic force of 300 mm/Hg without leaking but such large forces are not encountered in use.

The optimum angle y of the wiper from the longitudinal center axis of the plunger tip and optimum angle z of the wiper edge surface and optimum difference in the angles y and x of the leading and trailing surfaces of the wiper to achieve a thin wiper edge portion and a thicker base depends in part upon the stiffness of the material of the plunger tip.

It has been found that an angle y of 43°, (preferably it varies between about 20° and 65°, more preferably between about 30° and 50°) between the leading surface of the wiper and the longitudinal axis of the plunger tip and an angle x of 35° (preferably the difference over angle y may vary between about 10° and 30°, more preferably between about 4° and 15°) between the trailing surface and the longitudinal axis gives excellent results.

Excellent results can be achieved with a variety of needle sizes, particularly those from 20 to 22 gage. The speed with which the plunger tip moves is proportional to the needle gage size.

The aforesaid advantages of the syringe of this invention not only make it highly useful in an improved arterial blood sampling syringe but also for epidural anaesthesia employing the loss of resistance technique and it has been used successfully clinically for that purpose.

While the present syringe is particularly suitable for taking arterial blood samples and for epidural anaesthesia, its suitability for other functions will be readily appreciated in the art. It is disposable and inexpensive. It can be cheaply mass produced out of inexpensive raw materials. There are no breakage problems.

It is not intended that the invention be limited to or by the aforesaid description and accompanying drawings of only one embodiment thereof but only to the subject matter claimed hereinafter and its equivalents. It is understood that those skilled in the art will be enabled by the disclosure herein to make changes and modifications within the spirit and scope of this invention.

I claim:

1. A disposable syringe particularly suited to be used for obtaining a blood sample from a patient because of the low force requirement for the operation thereof, said syringe comprising:
   a barrel having a generally cylindrical inner wall comprising a working section thereof extending from a forward end of said barrel to a predetermined point, the inner diameter of said working section of said barrel being tapered radially inwardly in a direction from the forward end portion of said barrel toward said predetermined point; and
   a plunger comprising a plunger stem and a generally cylindrical plunger tip having an annular, elastically deformable wiper extending peripherally to engage said tapered working section of the inner wall to form a seal;
   wherein said syringe assembly comprises means for preventing further inward movement of said plunger to define a chamber having a predetermined volume for retaining a desired quantity of anticoagulant.

2. A disposable syringe particularly suited to be used for obtaining a blood sample from a patient because of the low force requirement for operation thereof, said syringe comprising:
   a barrel having a generally cylindrical inner wall comprising a working section thereof extending from a forward end of said barrel to a predetermined point, the inner diameter of said working section of said barrel being tapered radially inwardly from the forward end of said barrel to said predetermined point; and
   a plunger comprising a plunger stem and a compressible, elastomeric, generally cylindrical plunger tip of lesser diameter than the inner wall of said barrel, said plunger tip having an integral, annular, elastically deformable wiper extending peripherally radially outwardly and axially forwardly from said plunger tip at a forward portion thereof at an acute angle to the longitudinal center axis of said plunger tip and terminating at the outer edge thereof in a wiping edge having a minimal diameter slightly in excess of the diameter of the inner wall of said barrel, thereby forming a sealing engagement with the inner wall of said barrel, said annular wiper being the sole sealing element between said plunger tip and said wall;
   wherein said syringe assembly comprises means for preventing further inward movement of said plunger to define a chamber having a predetermined volume for retaining a desired quantity of anticoagulant.

3. A disposable syringe particularly suited to be used for obtaining a blood sample from a patient because of the low force requirement for operation thereof, said syringe comprising:
   a barrel having a generally cylindrical innner wall comprising a working section thereof extending from a forward end of said barrel to a predetermined point, the inner diameter of said working section of said barrel being tapered raially inwardly from the forward end of said barrel to said predetermined point; and
   a plunger comprising a plunger stem and a compressible, elastomeric, generally cylindrical plunger tip of lesser diameter than the inner wall of said barrel, said plunger tip having an integral, annular, elastically deformable wiper extending peripherally radially outwardly and axially forwardly from said plunger tip at a forward portion thereof at an acute angle to the longitudinal center axis of said plunger tip and terminating at the outer edge thereof in a wiping edge having a minimal diameter slightly in excess of the diameter of the inner wall of said barrel, thereby forming a sealing engagement with the inner wall of said barrel, said annular wiper being the sole sealing element between said plunger tip and said wall;

wherein said plunger tip has a plurality of raised portions spaced circumferentially around said plunger tip and located at the rearward portion of said plunger tip, said raised portions engaging said inner wall of said barrel with a minimum of frictional contact to prevent canting of said plunger tip in said barrel.

4. The syringe of claim 3, wherein said raised portions are conical in shape.

5. A disposable syringe particularly suited to be used for obtaining a blood sample from a patient because of the low force requirement for operation thereof, said syringe comprising:

a barrel having a generally cylindrical inner wall comprising a working section thereof extending from a forward end of said barrel to a predetermined point, the inner diameter of said working section of said barrel being tapered radially inwardly from the forward end of said barrel to said predetermined point;

a plunger comprising a plunger stem and a compressible, elastomeric, generally cylindrical plunger tip of lesser diameter than the inner wall of said barrel, said plunger tip having an integral, annular, elastically deformable wiper extending peripherally radially outwardly and axially forwardly from said plunger tip at a forward portion thereof at an acute angle to the longitudinal center axis of said plunger tip and terminating at the outer edge thereof in a wiping edge having a minimal diameter slightly in excess of the diameter of the inner wall of said barrel, thereby forming a sealing engagement with the inner wall of said barrel, said annular wiper being the sole sealing element between said plunger tip and said wall;

means for preventing further inward movement of said plunger to define a chamber having a predetermined volume for retaining a desired quantity of anticoagulant; and means for stopping outward movement of said plunger at said predetermined point when drawing said blood sample;

said plunger tip having a plurality of raised portions spaced circumferentially around said plunger tip and located at the rearward portion of said plunger tip, said raised portions engaging said inner wall of said barrel with a minimum of frictional contact to prevent canting of said plunger tip in said barrel.

6. The syringe of claim 5, wherein the inner diameter of the barrel in said working section is tapered to an extent that the inner diameter at the forward end of said barrel is no more than about 1.5 percent larger than the inner diameter of said barrel at said predetermined point.

7. The syringe of claim 5, wherein said wiper is tapered from the base thereof to the free end thereof so that it is thicker at its base than at its end.

8. The syringe of claim 7, wherein the angle between the leading surface of said wiper and the longitudinal axis of said plunger is between about 20° and 65° and the angle of the taper is between about 4° and 30°.

* * * * *